United States Patent [19]

Spencer

[11] Patent Number: 4,723,943
[45] Date of Patent: Feb. 9, 1988

[54] SHEATHED SYRINGE

[75] Inventor: John E. Spencer, Great Falls, Mont.

[73] Assignee: Montana Deaconess Medical Center, Great Falls, Mont.

[21] Appl. No.: 948,367

[22] Filed: Dec. 31, 1986

[51] Int. Cl.⁴ ............................................. A61M 5/32
[52] U.S. Cl. .................................... 604/198; 604/263
[58] Field of Search ............... 604/198, 197, 192, 263

[56] References Cited

U.S. PATENT DOCUMENTS 2,571,653  10/1951  Bastien ................................. 604/198
3,890,971   6/1975  Leeson et al. ...................... 604/197
4,425,120   1/1984  Sampson et al. .................... 604/198

Primary Examiner—John D. Yasko
Attorney, Agent, or Firm—Sughrue, Mion, Zinn, Macpeak, and Seas

[57] ABSTRACT

A syringe with a body and a needle at one end and an injection plunger movable into the body at the opposite end. A guide lug is fixed on the syringe body near the needle end. A sheath is positioned over the syringe body with a longitudinal groove that engages the guide lug. The sheath is movable with respect to the syringe body and guided by the lug so that it can selectively cover or expose the needle while not impeding use of the syringe.

11 Claims, 4 Drawing Figures

ROTATE TO TEMPORARY

ROTATE TO LOCK

SHEATHED SYRINGE

BACKGROUND OF THE INVENTION

This invention relates to a syringe and in particular to a syringe having an integral retractable sheath.

Syringes are used for injections, obtaining fluid samples and general laboratory utilization. Generally, as manufactured, syringes are packed with a disposable, removable sheath. Once the sheath is removed from the needle it may be discarded or lost such that the needle remains exposed. The syringe, if a plastic body, is generally discarded following use. If a glass body, the syringe may sometimes be sterilized and reused. In either case, following use, the needle may be recapped which leads to the dangers of self-inflicted needle sticks.

While disposal would appear to be straightforward, a number of problems occur. Most common is that the exposed and contaminated needle not infrequently scratches or wounds some member of the health care team, e.g., physicians, nurses or those individuals handling trash. For this reason a myriad of devices such as "needle boxes" and the like have evolved to safely dispose of syringes and/or needles. The use of those devices is often inconvenient and expensive such that in many facilities they are ignored or nonexistent.

Even when conveniently located in the patient's room or near the application site, many professionals have been trained to recap the needle with the removable sheath to prevent inadvertent needle sticks. Some health care professionals also recap needles to protect themselves. Additionally, they snap off the needle to prevent reuse by drug abusers who might avail themselves of this supply.

The need to protect individuals from any inadvertent contact from needles has become increasingly important with the many diseases (e.g., hepatitis, aids, etc.) that can be transmitted in this manner. The trend to return patients to their home environment as soon as possible has also increased the possibility that a friend or family member might also be at risk for exposure to a contaminated needle.

In the case of syringes that are to be reused, a requirement exists to sheath the needle when the device is being processed for reuse. If the original sheath is discarded a new one must be obtained. The requirement for maintaining a separate inventory of components makes the reuse of syringes expensive and time consuming.

SUMMARY OF THE INVENTION

Given the problems and challenges of proper syringe and needle disposal, it is an object of this invention to provide a syringe having an integral sheath to facilitate user protection from inadvertent needle sticks prior to proper disposal.

Yet another object of this invention is to provide a sheath that is retractable about a syringe body.

A further object of this invention is to provide a sheathed syringe having a snap lock to maintain the sheath in an extended position covering the needle.

These and other objects of this invention are accomplished by means of a sheath mounted coaxially on a syringe body. The syringe body has a projecting stationary guide lug that also serves as a locking lug. The sheath has a guide slot through which the guide projects. One end of the slot has a transverse opening. When the guide lug is located in the opening and either the sheath or syringe body are rotated with respect to each other, the sheath will be locked with respect to the syringe in a position covering the needle. The sheath further includes a series of annular gripping ridges at one portion and a retracting flange on one end.

The locking mechanism comprises one transverse opening engaging the guide lug in one position to temporarily lock the sheath and a second transverse opening providing a positive lock. Both openings extend perpendicular to and from the same end of the guide slot.

These and other aspects of this invention will be explained in greater detail by reference to the accompanying drawings and the description of the preferred embodiment that follows.

DESCRIPTION OF THE PREFERRED EMBODIMENT

Figure 1A:
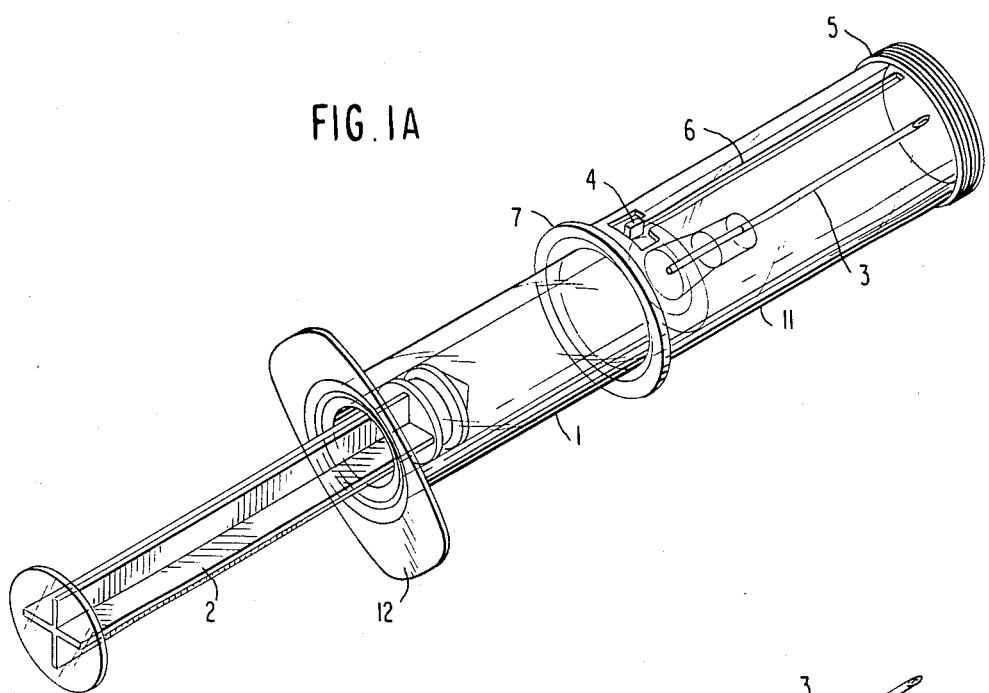
FIGS. 1A and 1B are isometric views of the syringe of this invention illustrating the extended and retracted positions of the sheath.
Figure 1B:
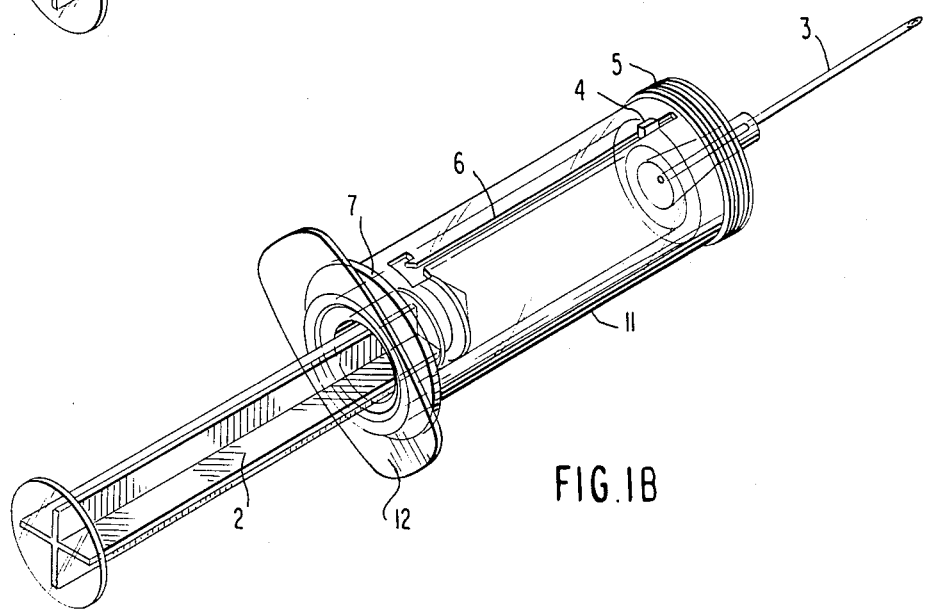

Referring now to FIGS. 1A and 1B, the basic components constituting this invention are illustrated. the calibrated hollow syringe body 1 is a transparent glass or plastic. The body 1 has a plunger 2 insertd into the hollow cavity and a needle at the opposite end thereof. Illustrated but not numbered are the other conventional elements such as the flexible plunger seal and external finger grips.

This invention departs from conventional syringe devices in that the body includes a fixed guide lug 4 positioned on the outer periphery near the needle end of the body 1. The guide lug 4, as will be explained herein, serves several functions. The lug 4 may be an integral part of the syringe body if molded, or added to existing syringe bodies as a modification thereof. The lug 4, while illustrated as being substantially rectangular may be any shape so long as it allows relative movement with the guide slot 6 on the sheath 11.

Figure 2:
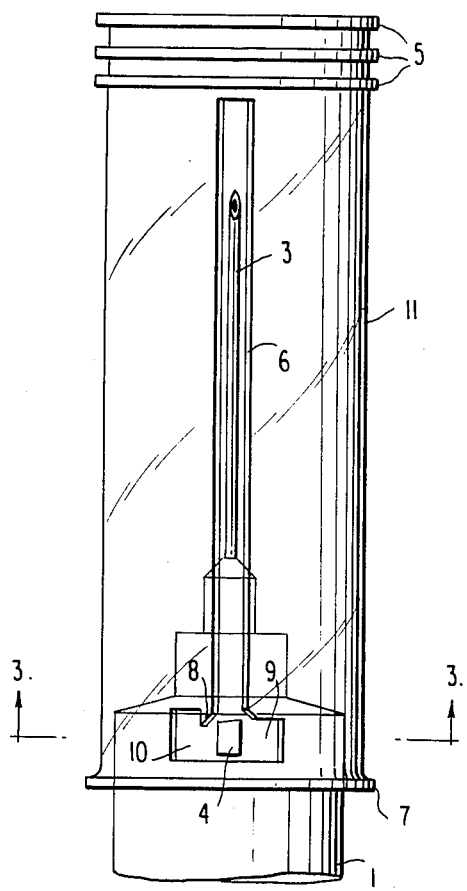
FIG. 2 is a partial top view of the syringe illustrating the details of the guide slot.

The guide slot 6 extends longitudinally along the barrel of the needle sheath 11 and terminates at the inner end with a circumferentially extending enlarged portion. As illustrated in FIG. 2, on one side of the guide slot 6, a temporary lock 9 is provided for the guide lug 4. At the opposite side of the guide slot 6, a snap lock lip 8 separates the guide slot from a positive lock area 10.

The needle sheath 11 has at its outer end a series of circumferential gripping ridges 5. At the opposite, or inner end, a retracting flange 7 is positioned. The ridges provide the necessary surface area discontinuities to permit rotation of the sheath 11 relative to the syringe 1 end therefore also to guide lug 4. Thus, when the sheath is in a position as illustrated in FIG. 1A, the sheath may be gripped and rotated while the end of the needle 3 is covered. To retract the sheath, a compressive force is applied between the retracting flange 7 and the syringe finger grips 12. During this motion, while the needle is being progressively exposed, there is no contact of the outer end of the sheath.

Figure 3:
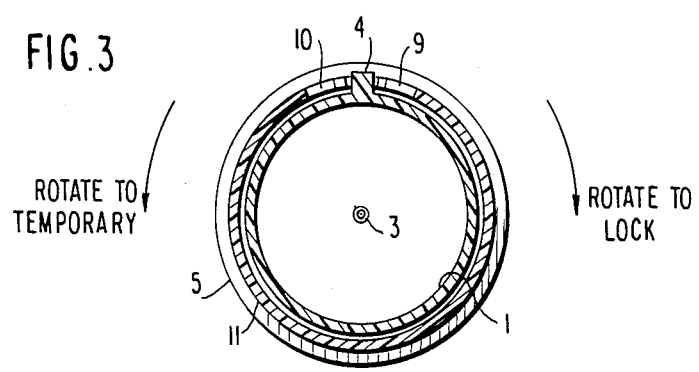
FIG. 3 is a sectional view of the syringe taken along line 3—3 of FIG. 2.

In operation, the device is stored with the syringe as illustrated in FIG. 1A except that the sheath is rotated clockwise so that the guide lug 4 is positioned in the positive lock area 10. The plunger may be pushed into the syringe body, but generally when unfilled, the plunger will be positioned as illustrated. To use, the barrel will be rotated, using the ridges 5, to align the guide lug 4 with the slot 6. Then, the sheath is retracted using the flange 7 to expose the needle. As illustrated in FIG. 3, the guide lug 4, due to its size, will engage the lock lip such that rotation of the sheath to "unlock" it requires sufficient force to deflect the lip 8. This insures that accidental rotation will not result in axial movement of the sheath. Once aligned with the slot 6, as illustrated in FIG. 2, the sheath can move axially with respect to the syringe. Once the procedure is completed, the sheath 11 is then extended to cover the needle. If only temporary locking is needed the sheath is rotated counterclockwise so that the guide lug 4 frictionally engages the temporary lock opening 9. During all operations the syringe and sheath remain an integral unit so that problems in the prior art with loss of the needle cap is avoided. Thus, this invention provides a simple yet effective syringe unit that offers improved safety.

It is apparent that modifications to this invention may be practiced without departing from the essential scope of the invention.

I claim:

1. A syringe comprising:
    a syringe body having a needle at one end and an injection plunger movable into said body at the opposite end,
    a guide lug fixed on said syringe body, and
    a sheath positioned over said syringe body, said sheath having a groove engaging said guide lug, means to lock said guide lug and prevent movement of said sheath when said needle is covered comprising an opening communicating with said groove and extending transverse thereto, said groove engaging and restraining said guide lug, said opening comprising a first portion having a deformable retaining lip to positively lock said guide lug and a second portion that frictionally engages said guide lug whereby said sheath is movable with respect to said syringe body and is guided by said lug in said groove to selectively cover and expose said needle while not impeding use of said syringe.

2. The syringe of claim 1, wherein said first and second portions extend respectively from opposite sides of said groove.

3. The syringe of claim 1, wherein said sheath further comprises a series of gripping edges at one end of said sheath.

4. The syringe of claim 1, wherein said sheath further comprises a retracting flange at one end thereof.

5. The syringe of claim 1, wherein said sheath further comprises a series of gripping ridges at one end and a retracting flange at the other end thereof.

6. A syringe unit comprising:
    a syringe body having a guide lug disposed on the outer periphery and,
    a sheath disposed over said syringe body and having a guide groove coacting with said guide lug to permit movement of said sheath relative to said syringe body,
    means to lock said guide lug and prevent movement of said sheath when said needle is covered comprising an opening communicating with said groove and extending transverse thereto, said groove engaging and restraining said guide lug, comprising a first portion having a deformable retaining lip to positively lock said guide lug and a second portion that frictionally engages said guide lug.

7. The syringe of claim 6, wherein said first and second portions extend respectively from opposite sides of said groove.

8. The syringe of claim 6, wherein said first and second portions extend respectively from opposite sides of said groove.

9. The syringe of claim 6, wherein said sheath further comprises a series of gripping edges at one end of said sheath.

10. The syringe of claim 6, wherein said sheath further comprises a retracting flange at one end thereof.

11. The syringe of claim 6, wherein said sheath further comprises a series of gripping ridges at one end and a retracting flange at the other end thereof.

* * * * *